US012558067B2

(12) United States Patent
    Davidsen

(10) Patent No.: US 12,558,067 B2
(45) Date of Patent: Feb. 24, 2026

(54) TEMPERATURE INSENSITIVE BACKING STRUCTURE FOR INTRALUMINAL IMAGING DEVICES

(71) Applicant: KONINKLIJKE PHILIPS N.V., Eindhoven (NL)

(72) Inventor: Richard Edward Davidsen, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 170 days.

(21) Appl. No.: 18/507,141

(22) Filed: Nov. 13, 2023

(65) Prior Publication Data

US 2024/0074732 A1    Mar. 7, 2024

Related U.S. Application Data

(63) Continuation of application No. 16/338,798, filed as application No. PCT/EP2017/075052 on Oct. 3, 2017, now Pat. No. 11,813,116.

(Continued)

(51) Int. Cl.
    *A61B 8/00*        (2006.01)
    *A61B 8/12*        (2006.01)
(52) U.S. Cl.
    CPC .............. *A61B 8/4494* (2013.01); *A61B 8/12* (2013.01); *A61B 8/4466* (2013.01); *A61B 2562/12* (2013.01)
(58) Field of Classification Search
    CPC ....... A61B 8/4494; A61B 8/12; A61B 8/4466; A61B 2562/12
    See application file for complete search history.

(56) References Cited

U.S. PATENT DOCUMENTS

| | | | |
|---|---|---|---|
| 8,975,713 B2 | 3/2015 | Sako et al. | |
| 2003/0149363 A1* | 8/2003 | Dreschel ................... | B06B 1/00 |
| | | | 600/437 |

(Continued)

FOREIGN PATENT DOCUMENTS

| | | | | |
|---|---|---|---|---|
| JP | 4137328 B2 * | 8/2008 | ......... | H01L 21/8221 |
| JP | 2014087556 A | 5/2014 | | |

(Continued)

OTHER PUBLICATIONS

Sun et al., High performance epoxy resin with ultralow coefficient of thermal expansion cured by conformation-switchable multi-functional agent, Chemical Engineering Journal, vol. 450, Part 3, 2022, 138295, ISSN 1385-8947, https://doi.org/10.1016/j.cej.2022.138295 (Year: 2022).*

(Continued)

*Primary Examiner* — John D Li

(57)        ABSTRACT

An imaging catheter assembly is provided. In one embodiment, the imaging catheter assembly includes a flexible elongate member including a distal portion and a proximal portion; and an imaging component coupled to the distal portion of the flexible elongate member, wherein the imaging component includes: an integrated circuit (IC) layer that includes a semiconductor material; an array of ultrasound transducer elements coupled to a first side of the IC layer; and a backing layer coupled to a second side of the IC layer opposite the first side, wherein the backing layer includes a backing material, and wherein a coefficient of thermal expansion (CTE) difference between the semiconductor material and the backing material is less than 23 parts per million per degree Centigrade (ppm/C).

17 Claims, 6 Drawing Sheets

Related U.S. Application Data

(60) Provisional application No. 62/437,724, filed on Dec. 22, 2016, provisional application No. 62/403,431, filed on Oct. 3, 2016.

(56) References Cited

U.S. PATENT DOCUMENTS

| | | | |
|---|---|---|---|
| 2005/0043625 | A1 | 2/2005 | Oliver et al. |
| 2005/0146247 | A1 | 7/2005 | Fisher et al. |
| 2008/0315331 | A1 | 12/2008 | Wodnicki et al. |
| 2011/0166455 | A1* | 7/2011 | Cully ................... A61B 8/4245 |
| | | | 600/463 |
| 2013/0031980 | A1 | 2/2013 | Sako et al. |
| 2013/0285174 | A1 | 10/2013 | Sako et al. |
| 2014/0050054 | A1 | 2/2014 | Toda et al. |
| 2015/0145374 | A1 | 5/2015 | Xu |
| 2015/0272548 | A1 | 10/2015 | Lu |
| 2015/0289851 | A1 | 10/2015 | Kobayashi et al. |
| 2016/0007961 | A1 | 1/2016 | Lee et al. |

FOREIGN PATENT DOCUMENTS

| | | |
|---|---|---|
| JP | 2015221214 A | 12/2015 |
| WO | 2011132531 A1 | 10/2011 |
| WO | 2016007250 A1 | 1/2016 |

OTHER PUBLICATIONS

The Engineering Toolbox, Metals—Temperature Expansion Coefficients (Year: 2025).*

Machine Translation of JP4137328B2 (Year: 2025).*

* cited by examiner

600

700

TEMPERATURE INSENSITIVE BACKING STRUCTURE FOR INTRALUMINAL IMAGING DEVICES

RELATED APPLICATIONS

This application is a continuation of U.S. application Ser. No. 16/338,798, filed on Apr. 2, 2019, now U.S. Pat. No. 11,813,116, which is the U.S. National Phase application under 35 U.S.C. § 371 of International Application No. PCT/EP2017/075052, filed on Oct. 3, 2017, which claims the benefit of and priority to U.S. Provisional Application No. 62/403,431, filed Oct. 3, 2016, and 62/437,724, filed Dec. 22, 2016, which are incorporated by reference in their entireties.

TECHNICAL FIELD

The present disclosure relates generally to intraluminal imaging devices and, in particular, to temperature insensitive backing structures for imaging arrays of intraluminal imaging devices.

BACKGROUND

Minimally invasive surgeries have been enabled by the advance of various medical technologies. For example, diagnostic and therapeutic ultrasound catheters have been designed for imaging inside areas of the human body. In the cardiovascular system, two common diagnostic ultrasound methods are intravascular ultrasound (IVUS) and intracardiac echocardiography (ICE). Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

IVUS catheters are typically used in the large and small blood vessels (arteries or veins) of the body, and are almost always delivered over a guidewire having a flexible tip. ICE catheters are usually used to image chambers of the heart and surrounding structures, for example, to guide and facilitate medical procedures, such as transseptal lumen punctures, left atrial appendage closures, atrial fibrillation ablation, and valve repairs. Commercially-available ICE catheters are not designed to be delivered over a guidewire, but instead have distal ends which can be articulated by a steering mechanism located in a handle at the proximal end of the catheter. For example, an ICE catheter may be inserted through the femoral or jugular artery when accessing the anatomy, and steered in the heart to acquire images necessary to the safety of the medical procedures.

An ICE catheter typically includes an ultrasound imaging component that generates and receives acoustic energy. The imaging component is encased in a tip assembly located at a furthest distal tip of the catheter. The tip assembly is covered with acoustic adhesive materials. An electrical cable is connected to the imaging component and extends through the core of the body of the catheter. The electrical cable may carry control signals and echo signals to facilitate imaging of the heart anatomy. The device may provide rotational, 2-way, or 4-way steering mechanisms such that anterior, posterior, left, and/or right views of the heart anatomy may be imaged.

Surface imaging components may include a matrix array of ultrasound transducers fabricated with an application-specific integrated circuit (ASIC) coupled to a backside of the matrix array opposite a front side of the matrix array where ultrasound waves are emitted. The matrix array can include a large number of ultrasound transducers (e.g., hundreds of ultrasound transducers). The matrix array can provide high-quality two-dimensional (2D) and three-dimensional (3D) imaging. The ASIC can be pitch-matched to the ultrasound transducers. The ASIC is typically formed from a silicon material. The ASIC can perform micro-beamforming on the ultrasound echo signals collected by the ultrasound transducers. The surface imaging components can include a de-matching layer and a backing layer to eliminate or reduce unwanted acoustic distortions. The de-matching layer typically has a thickness of about a quarter of a wavelength of the ultrasound waves. The de-matching layer can reflect forward ultrasound waves travelling toward the backside of the matrix array. The backing layer is typically formed from a polymeric material and has a thickness less than 1 centimeter (cm). The backing layer can disperse or dampen remaining backward travelling ultrasound waves.

For a given material, the degree of expansion during heating and contraction during cooling is represented by a coefficient of thermal expansion (CTE). The silicon material of the ASIC and the polymeric material of the backing layer have highly differentiating CTEs. In surface transducers, the backing layer can be made sufficiently thick so that the two continuous layers (e.g., the ASIC and the backing layer) of materials with highly differentiating CTEs may not cause surface transducers to warp or bend under thermal excursions, which may vary from about −20 degree Celsius (° C.) to about 60° C.

In order to fabricate matrix array transducers for catheter imaging, the form factor of the matrix array transducers is required to be significantly reduced. For example, catheter imaging components may be limited to a diameter about 3 millimeter (mm) for ICE devices and less than 3 mm for IVUS devices. Thus, the backing layer in a catheter imaging component is required to be significantly thinner than a surface imaging component. When the backing layer is thin, the varying CTEs between the ASIC and the backing layer can cause the catheter imaging component to warp or bend under thermal excursions. The bending can result in damages to the imaging component and provide poor reliability.

SUMMARY

The invention provides devices, systems, and related methods for providing intraluminal imaging components that overcome the limitations associated with previous designs.

Embodiments of the present disclosure provide an intraluminal imaging component with improved stability and reliability by reducing or eliminating thermal stress in the imaging component during thermal excursions. The imaging component includes an array of ultrasound transducer elements and a backing material layer coupled to opposite sides of an integrated circuit (IC) layer composed of a semiconductor material. In one embodiment, the thermal stress is reduced by selecting a backing material with a coefficient of thermal expansion (CTE) closer to the CTE of the semiconductor material of the IC layer but still provide sufficient acoustic attenuation. In another embodiment, the thermal stress is eliminated by adding an additional support layer with a similar material or the same material as the semiconductor material of the IC layer. The support layer is coupled to the backing layer opposite the IC layer. The addition of the support layer enables the backing layer to be constructed from a standard or commonly used backing material without compromising acoustic attenuation performance.

In one embodiment, an imaging catheter assembly is provided. The imaging catheter assembly includes a flexible elongate member including a distal portion and a proximal portion; and an imaging component coupled to the distal portion of the flexible elongate member, wherein the imaging component includes: an integrated circuit (IC) layer that includes a semiconductor material; an array of ultrasound transducer elements coupled to a first side of the IC layer; and a backing layer coupled to a second side of the IC layer opposite the first side, wherein the backing layer includes a backing material, and wherein a coefficient of thermal expansion (CTE) difference between the semiconductor material and the backing material is less than 23 parts per million per degree Centigrade (ppm/C).

In some embodiments, the backing material is selected from the group of materials consisting of high density particles in a hard epoxy matrix. In some embodiments, the backing material includes a CTE between 15 parts per million per degree Centigrade (ppm/C) and 25 ppm/C. In some embodiments, the backing layer provides an acoustic attenuation between 6 decibels per millimeter (dB/mm) to 3 dB/mm. In some embodiments, the backing layer includes a thickness less than 1.0 millimeter (mm). In some embodiments, the IC layer includes a thickness less than 0.2 millimeter (mm). In some embodiments, the imaging component further includes a support layer coupled to the backing layer opposite the IC layer. In some embodiments, the support layer is configured to balance a CTE-based stress in the imaging component. In some embodiments, the support layer includes a same material as the semiconductor material of the IC layer.

In one embodiment, an imaging catheter assembly is provided. The imaging catheter assembly includes a flexible elongate member including a distal portion and a proximal portion; and an imaging component coupled to the distal portion of the flexible elongate member, wherein the imaging component includes: an integrated circuit (IC) layer that includes a first material; an array of ultrasound transducer elements coupled to a first side of the IC layer; a backing layer coupled to a second side of the IC layer opposite the first side; and a support layer coupled to the backing layer opposite the IC layer, wherein the support layer includes a second material, and wherein a coefficient of thermal expansion (CTE) difference between the first material and the second material is less than 10 parts per million per degree Centigrade (ppm/C).

In some embodiments, the first material and the second material are the same material. In some embodiments, the first material and the second material include silicon. In some embodiments, the backing layer includes a thickness less than 1.0 millimeter (mm). In some embodiments, the support layer includes a thickness less than 1.0 millimeter (mm). In some embodiments, the IC layer includes a thickness less than 0.2 millimeter (mm).

In one embodiment, a method of manufacturing an imaging catheter assembly is provided. The method includes forming an imaging component by: providing an integrated circuit (IC) layer that includes a semiconductor material; coupling an array of ultrasound transducer elements to a first side of the IC layer; and coupling a backing layer to a second side of the IC layer opposite the first side, wherein the backing layer includes a backing material, and wherein a coefficient of thermal expansion (CTE) difference between the semiconductor material and the backing material is less than 23 parts per million per degree Centigrade (ppm/C); and coupling the imaging component to a distal portion of a flexible elongate member.

In some embodiments, the backing material is selected from the group of materials consisting of dense particles in epoxy matrices. In some embodiments, the backing layer includes a thickness less than 1.0 millimeter (mm). In some embodiments, the IC layer includes a thickness less than 0.2 millimeter (mm). In some embodiments, the method further comprises coupling a support layer to the backing layer opposite the IC layer. In some embodiments, the support layer includes a same material as the semiconductor material of the IC layer.

In one embodiment, a method of manufacturing an imaging catheter assembly is provided. The method includes forming an imaging component by: providing an integrated circuit (IC) layer that includes a first material; coupling an array of ultrasound transducer elements to a first side of the IC layer; coupling a backing layer to a second side of the IC layer opposite the first side; and coupling a support layer to the backing layer opposite the IC layer, wherein the support layer includes a second material, wherein a coefficient of thermal expansion (CTE) difference between the first material and the second material is less than 10 parts per million per degree Centigrade (ppm/C); and coupling the imaging component to a distal portion of a flexible elongate member.

In some embodiments, the first material and the second material are the same material. In some embodiments, the first material and the second material include silicon. In some embodiments, the backing layer includes a thickness less than 1.0 millimeter (mm). In some embodiments, the support layer includes a thickness less than 1.0 millimeter (mm). In some embodiments, the IC layer includes a thickness less than 0.20 millimeter (mm).

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
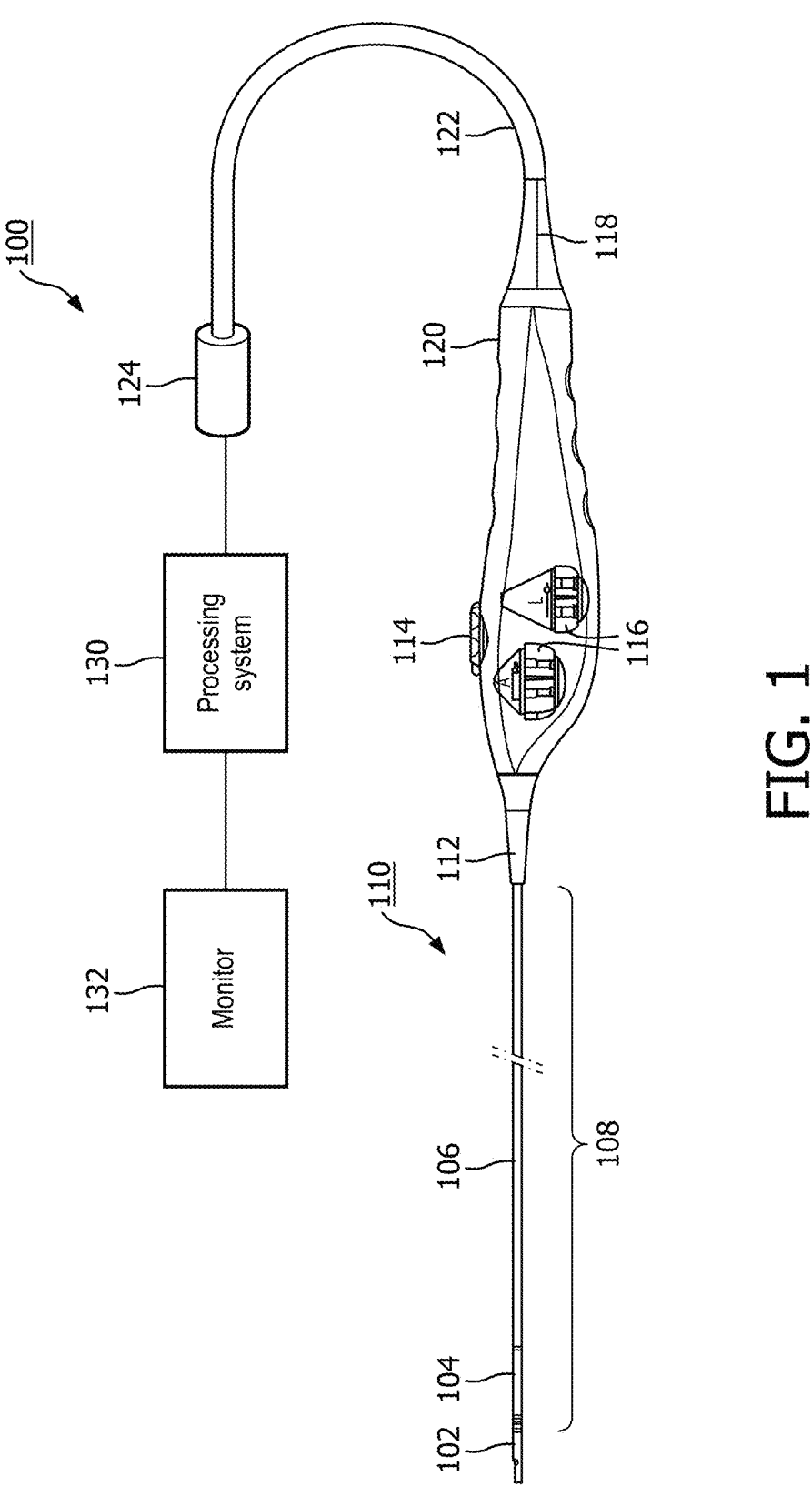
FIG. 1 is a schematic diagram of an intraluminal imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the intraluminal system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal imaging system 100 according to embodiments of the present disclosure. The system 100 may include an intraluminal device 110, a connector 124, a control and processing system 130, such as a console and/or a computer, and a monitor 132. The intraluminal device 110 includes a tip assembly 102, a flexible elongate member 108, and a handle 120. The flexible elongate member 108 includes a distal portion 104 and a proximal portion 106. The distal end of the distal portion 104 is attached to the tip assembly 102. The proximal end of the proximal portion 106 is attached to the handle 120 for example, by a resilient strain reliever 112, for manipulation of the intraluminal device 110 and manual control of the intraluminal device 110. The tip assembly 102 can include an imaging component with ultrasound transducer elements and associated circuitry. The handle 120 can include actuators 116, a clutch 114, and other steering control components for steering the intraluminal device 110. In an embodiment, the intraluminal device 110 is an ICE device.

The handle 120 is connected to the connector 124 via another strain reliever 118 and an electrical cable 122. The connector 124 may be configured in any suitable configurations to interconnect with the processing system 130 and the monitor 132 for processing, storing, analyzing, manipulating, and displaying data obtained from signals generated by the imaging core at the tip assembly 102. The processing system 130 can include one or more processors, memory, one or more input devices, such as keyboards and any suitable command control interface device. The processing system 130 can be operable to facilitate the features of the intraluminal imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician advances the flexible elongate member 108 into a vessel within a heart anatomy. The physician or clinician can steer the flexible elongate member 108 to a position near the area of interest to be imaged by controlling the actuators 116 and the clutch 114 on the handle 120. For example, one actuator 116 may deflect the tip assembly 102 and the distal portion 104 in a left-right plane and the other actuator 116 may deflect the tip assembly 102 and the distal portion 104 in an anterior-posterior plane. The clutch 114 provides a locking mechanism to lock the positions of the actuators 116 and in turn the deflection of the flexible elongate member 108 while imaging the area of interest.

The imaging process may include activating the ultrasound transducer elements on the tip assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the processing system 130 where the ultrasound image is reconstructed and displayed on the monitor 132. In some embodiments, the processing system 130 can control the activation of the ultrasound transducer elements and the repletion of the echo signals. In some embodiments, the processing system 130 and the monitor 132 may be part of the same system.

The system 100 may be utilized in a variety of applications such as transseptal lumen punctures, left atrial appendage closures, atrial fibrillation ablation, and valve repairs and can be used to image vessels and structures within a living body. In addition, the tip assembly 102 may include any suitable physiological sensor or component for diagnostic, treatment, and/or therapy. For example, the tip assembly can include an imaging component, an ablation component, a cutting component, a morcellation component, a pressure-sensing component, a flow-sensing component, a temperature-sensing component, and/or combinations thereof.

Figure 2:
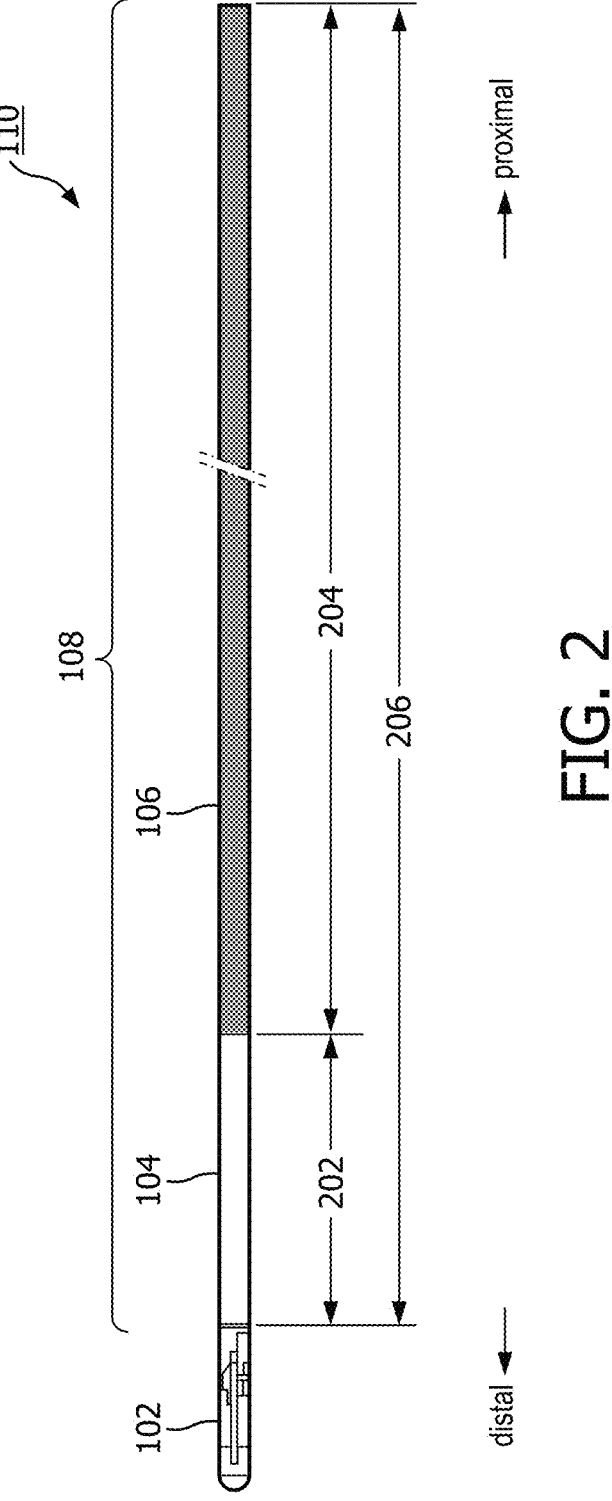
FIG. 2 is a schematic diagram of a portion of an intraluminal device according to embodiments of the present disclosure.

FIG. 2 is a schematic diagram of a portion of the intraluminal device 110 according to embodiments of the present disclosure. The tip assembly 102 and the flexible elongate member 108 are shaped and sized for insertion into vessels of a patient body. The flexible elongate member 108 can be composed of any suitable material, such as Pebax® polyether block amides. The distal portion 104 and the proximal portion 106 are tubular in shape and may include one or more lumens extending along a length of the flexible elongate member 108. In some embodiments, one lumen (e.g., a primary lumen) may be sized and shaped to accommodate an electrical cable 340 (shown in FIG. 3) interconnecting the tip assembly 102 and the connector 124 for transferring echo signals obtained from the transducer elements. In addition, the lumen may be shaped and sized to accommodate other components for diagnostic and/or therapy procedures. In some other embodiments, one or more lumens (e.g., secondary lumens) may be sized and shaped to accommodate steering wires, for example, extending from the distal portion 104 to the handle 120. The steering wires may be coupled to the actuators 116 and the clutch 114 such that the flexible elongate member 108 and the tip assembly 102 are deflectable based on actuations of the actuators 116 and the clutch 114. Dimensions of the flexible elongate member 108 can vary in different embodiments. In some embodiments, the flexible elongate member 108 can be a catheter having an outer diameter between about 8 and about 12 French (Fr) and can have a total length 206 between about 80 centimeters (cm) to about 120 cm, where the proximal portion 106 can have a length 204 between about 70 cm to about 118 cm and the distal portion 104 can have a length 202 between about 2 cm to about 10 cm.

Figure 3:
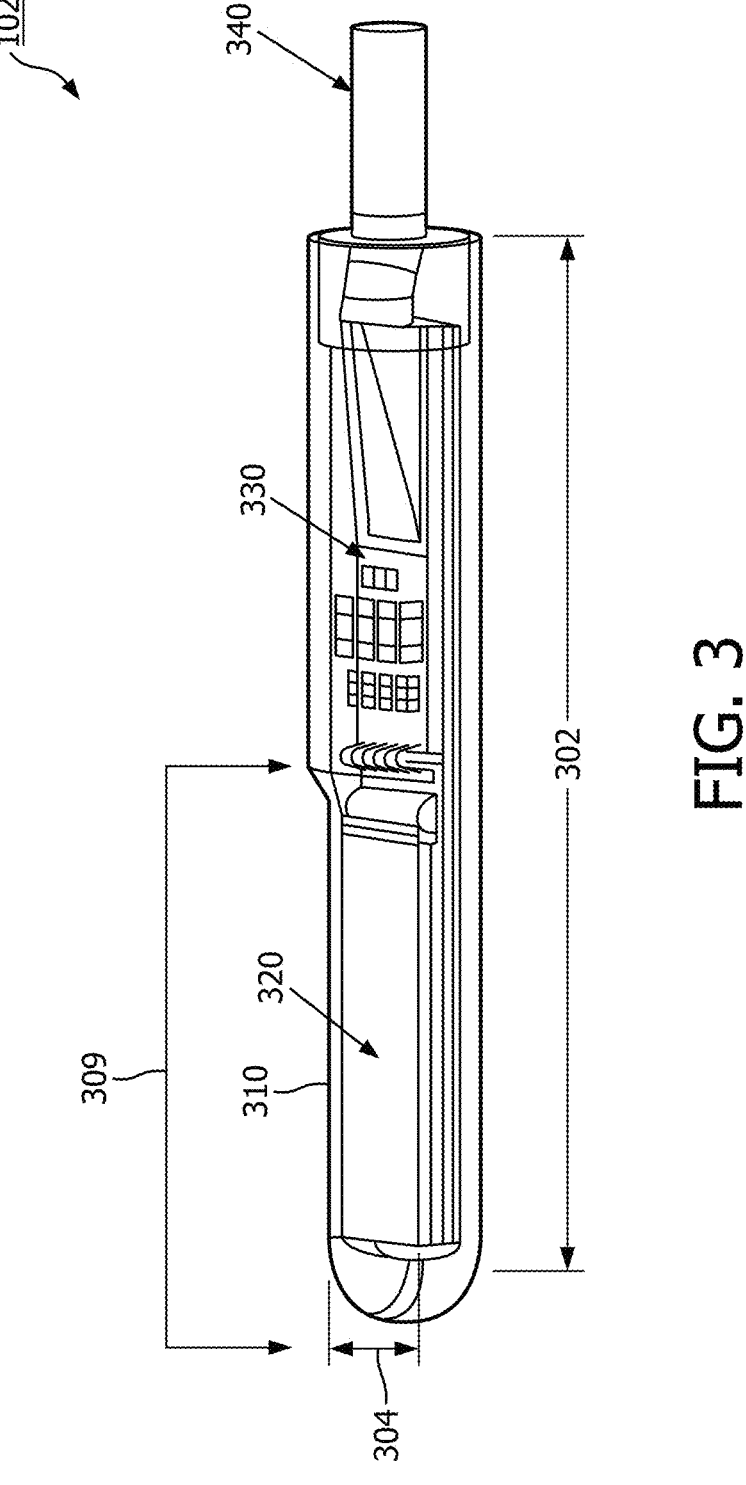
FIG. 3 is a schematic diagram of a tip assembly according to embodiments of the present disclosure.

FIG. 3 is a schematic diagram of the tip assembly 102 according to embodiments of the present disclosure. FIG. 3 provides a more detailed view of the tip assembly 102. The tip assembly 102 includes a tip member 310, an imaging component 320, and an interposer 330. The tip member 310 has a tubular or semi-tubular body sized and shaped for insertion into a patient body. The tip member 310 can be composed of a thermoplastic elastomer material or any suitable biocompatible material that has acoustic impedance matching to blood within a vessel of a patient body when in use. For example, the tip member 310 can be composed of Pebax® polyether block amides. Dimensions of the tip member 310 can vary in different embodiments and may depend on the size of the catheter or the flexible elongate member 108. In some embodiments, the tip member 310 can include a length 302 between about 15 millimeter (mm) to about 30 mm and a width 304 between about 2 mm to about 4 mm.

The interposer 330 interconnects the imaging component 320 to an electrical cable 340. The imaging component 320 emits ultrasound energy and receives ultrasound echo signals reflected by surrounding tissues and vasculatures. The imaging component 320 is described in greater detail herein with references to FIG. 4. The electrical cable 340 extends along a length of the flexible elongate member 108 and may be coupled to the cable 122. The electrical cable 340 carries the ultrasound echo signals to the processing system 130 for image generation and analysis. In addition, the electrical cable 340 can carry control signals for controlling the imaging component 320. Further, the electrical cable 340 can carry power for powering the imaging component 320.

Figure 4:
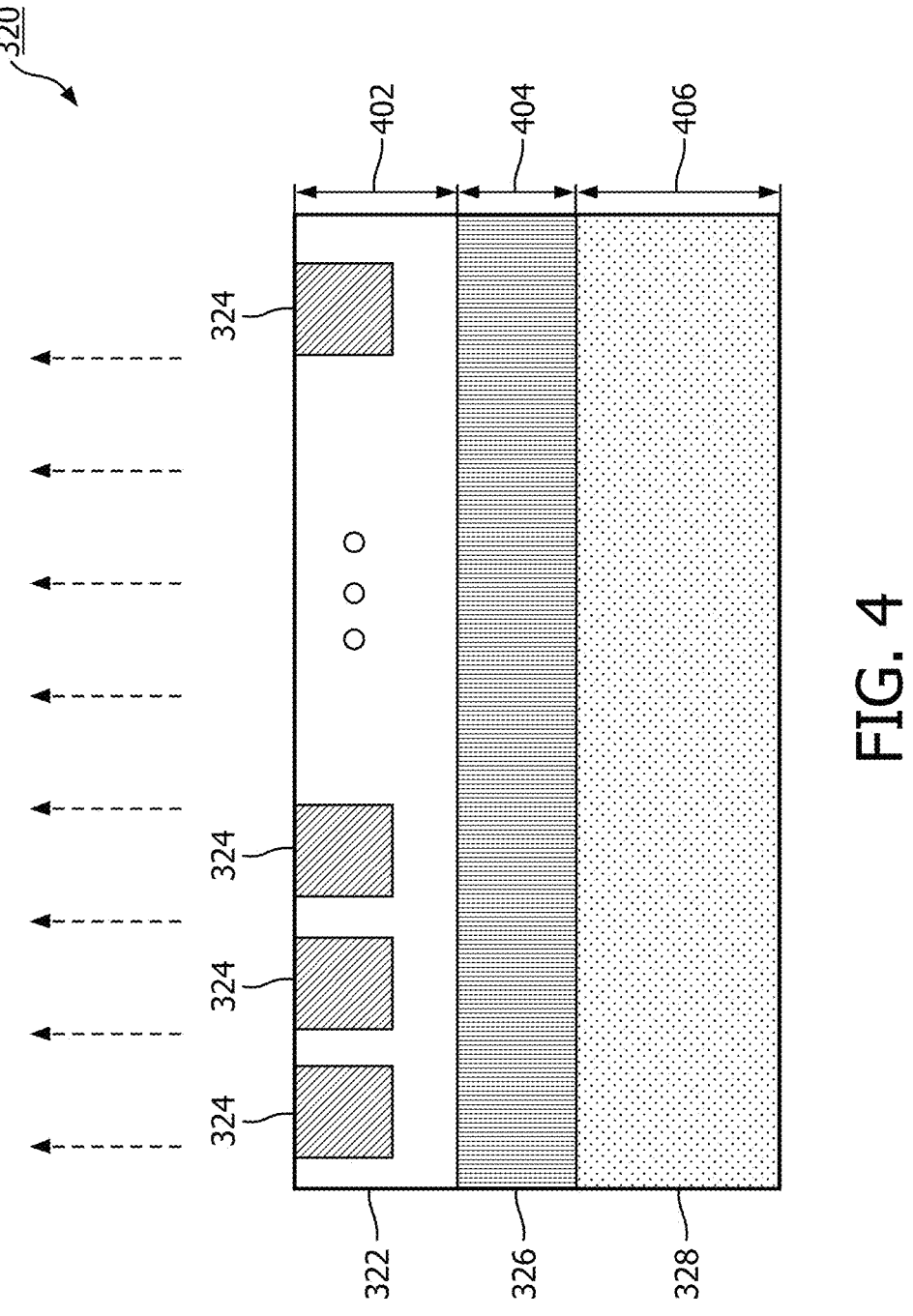
FIG. 4 is a cross-sectional view of an imaging according to embodiments of the present disclosure.

FIG. 4 is a cross-sectional view of the imaging component 320 taken along the line 309 of FIG. 3 according to embodiments of the present disclosure. The imaging component 320 is a planar component including an acoustic layer 322, an IC layer 326, and a backing layer 328. The acoustic layer 322 may include multiple layers of piezoelectric materials. The IC layer 326 is positioned between the acoustic layer 322 and the backing layer 328.

The acoustic layer 322 includes an array of ultrasound transducer elements 324. The ultrasound transducer elements 324 are composed of piezoelectric material. Exemplary transducers for ICE have a typical thickness of approximately 0.28 mm in the piezoelectric material to enable an 8 megahertz (MHz) ultrasound signal to be generated and transmitted at a typical velocity of 1500 meter per second (m/sec) through blood. The ultrasound signal may propagate in the direction as shown by the dashed arrows. The transducer thickness can be of various thicknesses ranging approximately from 0.56 mm to 0.19 mm to generate sufficient penetration depth in tissue imaging. In general, the thickness of the transducers can be adjusted for the frequency of sound in the transmission medium for the desired penetration depth in any tissue imaging. Image intensity can be adjusted by a driving voltage on the transducers.

In some embodiments, the acoustic layer 322 may include about 32 to about 128 ultrasound transducer elements 324 arranged in a one-dimensional (1D) pattern for two-dimensional (2D) imaging. In some embodiments, the acoustic layer 322 may include about 500 to about 1500 ultrasound transducer elements 324 arranged in a 2D pattern for three-dimensional (3D) imaging.

The IC layer 326 includes an application-specific integrated circuit (ASIC) formed from a semiconductor material, such as silicon. The ASIC may multiplex control signals, for example, generated by the processing system 130, and transfer the control signals to corresponding ultrasound transducer elements 324. The controls signals can control the emission of ultrasound pulses and/or the reception of echo signals. In the reverse direction, the ASIC may receive ultrasound echo signals reflected by target tissue and received by the ultrasound transducer elements 324. The ASIC may convert the ultrasound echo signals into electrical signals and transfer the electrical signals through the interposer 330 and the electrical cable 340 to the processing system 130 for processing and/or display. The ASIC may perform signal conditioning before transferring the signals. Signal conditioning may include filtering, amplification, and beamforming.

The backing layer 328 is composed of an acoustically absorptive material so that the backing layer 328 can absorb or deaden the ultrasonic waves coming from the back of the acoustic layer 322. The backing layer 328 may be composed of a polymeric material. Some examples of commonly used backing materials may include Boron Nitride particles in an epoxy matrix.

Dimensions of the imaging component 320 may vary in different embodiments and may be dependent on the size of the tip member 310. For example, the acoustic layer 322 can have a thickness 402 between about 0.3 mm to about 0.9 mm. The IC layer 326 can have a thickness 404 between about 0.05 mm to about 0.20 mm. The backing layer 328 can have a thickness 406 between about 0.20 mm to about 1.0 mm.

As described above, the IC layer 326 is commonly constructed from a silicon material, which has a low CTE (e.g., about 2.6 parts per million per degree Centigrade (ppm/C)). However, the polymeric material of the backing layer 328 is typically constructed from a polymeric material with a high CTE of about 63 to provide an acoustic attenuation of about 6 decibel per millimeter (dB/mm). Thus, the IC layer 326 and the backing layer 328 have a CTE difference of about 60. The highly differentiating CTEs between the two continuous thin layers (e.g., the IC layer 326 and the backing layer 328) can cause the imaging component 320 to warp or bend under thermal excursions. For example, temperature may vary from about –20 degree Celsius (° C.) to about 60° C. during shipping and storage of the imaging component 320.

In an embodiment, to reduce CTE-based stress (e.g., warping and bending) under thermal excursions, a material with a CTE closer to the CTE of the silicon material of the IC layer 326 is selected for the backing layer 328. Developing a material with a same CTE or a similar CTE as the silicon material of the IC layer 326 and having a sufficient amount of acoustic attenuation may be difficult due to the competing structural, process, and acoustic requirements of the imaging component 320. One approach to providing an imaging component with a better thermal stress-balance is to select or develop a backing material with a CTE better matched to the CTE of the IC layer 326, but may compromise for a lower acoustic attenuation. The following table shows some example backing materials that may be used to construct the backing layer 328:

TABLE 1

| Example Backing Materials | | | |
|---|---|---|---|
| Backing material | Material A Standard | Material B Lower CTE | Material C Lowest CTE |
| CTE (ppm/C) | 63 | 25 | 15 |
| Attenuation (relative to standard backing) | 1.0 | 0.4 | 0.05 |

The material A is a standard or commonly used backing material with a CTE of about 63 ppm/C. The material A can provide an acoustic attenuation of about 6 dB/mm. Some examples of the material A may include Boron Nitride particles in a soft epoxy matrix. The material B has a reduced CTE of about 25 ppm/C and can provide an acoustic attenuation of about 3 dB/mm. Some examples of the material B may include Graphite particles in an epoxy matrix. The material C has a further reduced CTE of about 15 ppm/C and can provide an acoustic attenuation of about 0.4 dB/mm. Some examples of the material C may include Alumina particles in a hard epoxy matrix. The material A can provide the best acoustic attenuation for the imaging component 320, but can cause bending during thermal excursions. The material B has a good compromise between CTE matching and acoustic attenuation. The material B can reduce the CTE difference between the IC layer 326 and the backing layer 328 from about 60 ppm/C to about 22 ppm/C and can provide about 40 percent (%) of the acoustic attenuation when compared to the material A. The material C can reduce the CTE difference to about 12 ppm/C and can provide about 5% of the acoustic attenuation when compared to the material A. Thus, the backing material for the backing layer 328 can be selected based on particular transducer requirements to trade-off between acoustic attenuation and CTE-based stress.

Figure 5:
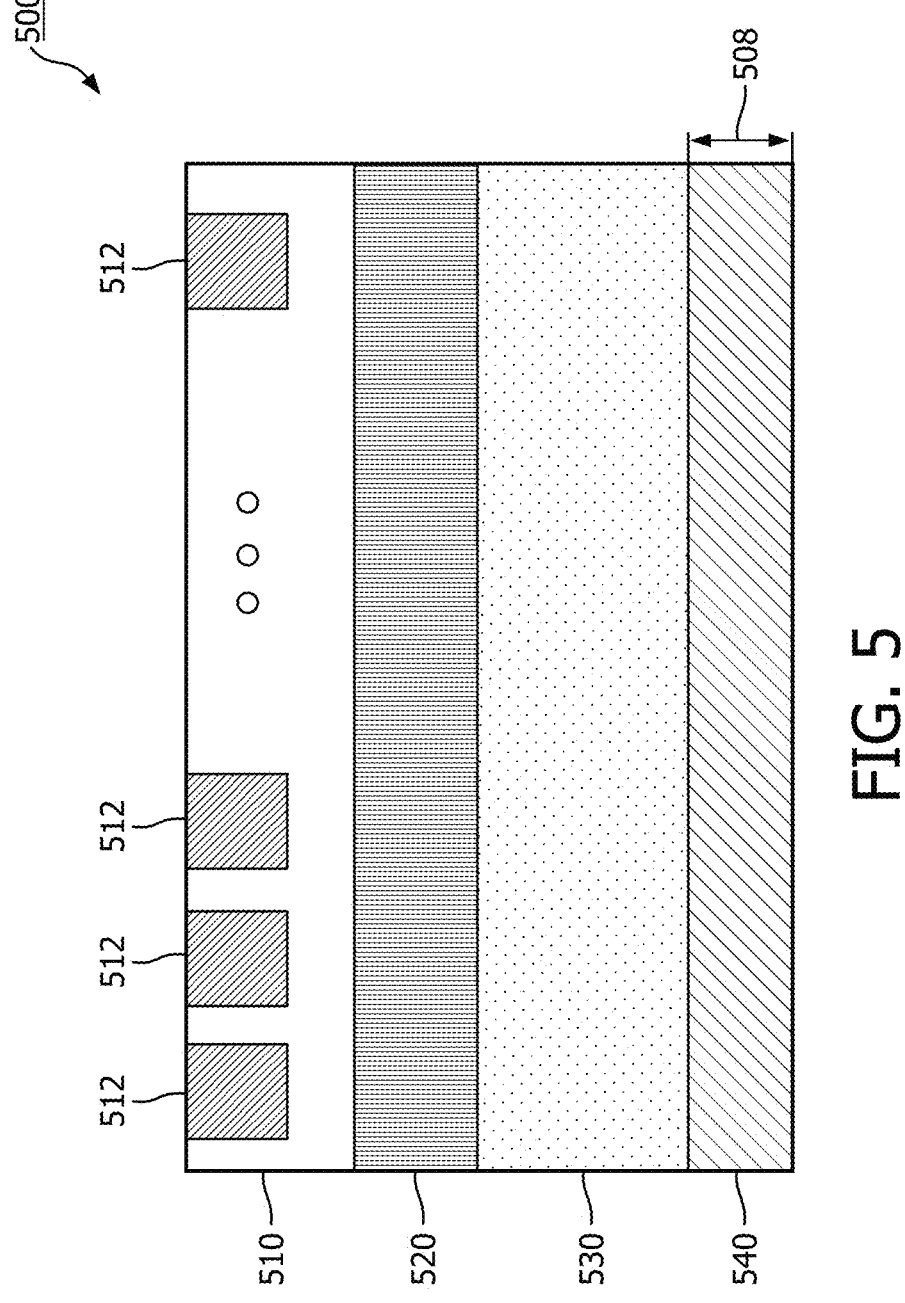
FIG. 5 is a cross-sectional view of an imaging including a support layer according to embodiments of the present disclosure.

FIG. 5 is a cross-sectional view of an imaging component 500 including a support layer 540 according to embodiments of the present disclosure. The imaging component 500 can be employed by the tip assembly 102 in place of the imaging component 320. The cross-sectional view is taken along the line 309 of FIG. 3. The imaging component 500 is substantially similar to the imaging component 320, but includes the additional support layer 540. As shown, the imaging component 500 includes an acoustic layer 510, an IC layer 520, a backing layer 530, and a support layer 540. The acoustic layer 510 is similar to the acoustic layer 322. The acoustic layer 510 includes any array of ultrasound transducer elements 512 similar to the ultrasound transducer elements 324. The IC layer 520 is similar to the IC layer 326. The backing layer 530 is similar to the backing layer 530, but may include a different backing material. The support layer 540 is attached to a bottom side of the backing layer 530 opposite the IC layer 520. The support layer 540 may be a thin layer composed of a similar material or the same material as the IC layer 520. As such, the support layer 540 can have a similar CTE or the same CTE as the IC layer 520. Thus, the support layer 540 can balance CTE-based stress in the imaging component 500. The addition of the support layer 540 enables the backing layer 530 to be constructed from the same standard or commonly used backing material. Thus, the imaging component 500 can provide the same acoustic attenuation performance as imaging components with standard backing materials and eliminate bending during thermal excursions.

Dimensions of the imaging component 500 can vary in different embodiments. In some embodiments, the acoustic layer 510, the IC layer 520, and the backing layer 530 can have similar thicknesses as the acoustic layer 322, the IC layer 326, and the backing layer 328. The support layer 540 can have a thickness 508 between about 0.05 mm to about 1.0 mm. When the support layer 540 is constructed from the same material as the IC layer 520, the support layer 540 and the IC layer 520 can have about the same thickness, which may provide a perfect balance with no warping regardless of temperature. When the support layer 540 is thinner than the IC layer 520, the support layer 540 may be constructed from a stiffer material with a lower CTE than the IC layer 520 in order to perfectly balance the bending forces that may occur due to temperature changes.

Figure 6:
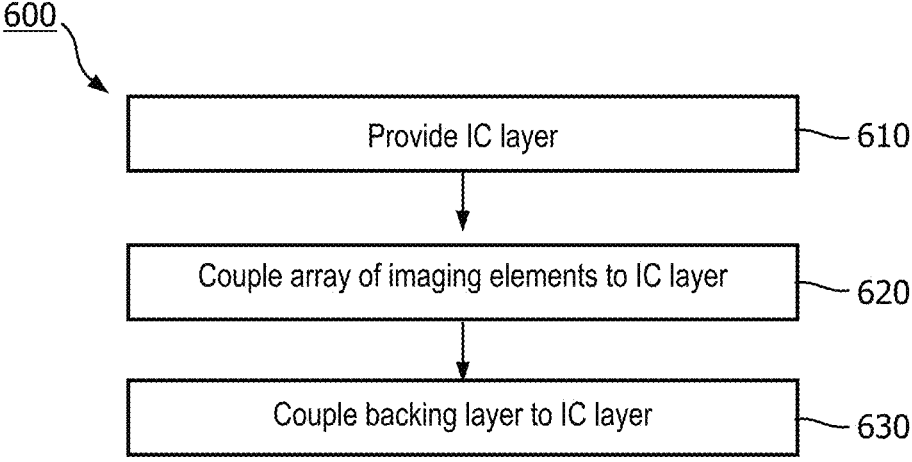
FIG. 6 is a flow diagram of a method of manufacturing an imaging component according to embodiments of the present disclosure.

FIG. 6 is a flow diagram of a method 600 of manufacturing the imaging component 320 according to embodiments of the present disclosure. It is understood that additional steps can be provided before, during, and after the steps of method 600, and some of the steps described can be replaced or eliminated for other embodiments of the method. The steps of the method 600 can be carried out by a manufacturer of a catheter in the order as shown or in any suitable order (e.g., in a reverse order).

At step 610, the method 600 includes providing an IC layer (e.g., the IC layer 326). The IC layer can be constructed from a semiconductor material (e.g., silicon). At step 620, the method 600 includes coupling an array of ultrasound transducer elements (e.g., the ultrasound transducer elements 324) to the IC layer. At step 630, the method 600 includes coupling a backing layer (e.g., the backing layer 328) to the IC layer opposite the array of ultrasound transducer elements. The backing layer can be constructed from a backing material. The backing material can be selected such that the CTE of the backing material is close to the CTE of the material of the IC layer. For example, a CTE difference between the semiconductor material of the IC layer and the backing material of the backing layer may be less than 23 ppm/C. In some embodiments, the backing material may have a CTE between about 15 ppm/C to about 25 ppm/C. The backing material can be selected from the group of materials consisting of high density particles in a hard epoxy matrix.

Figure 7:
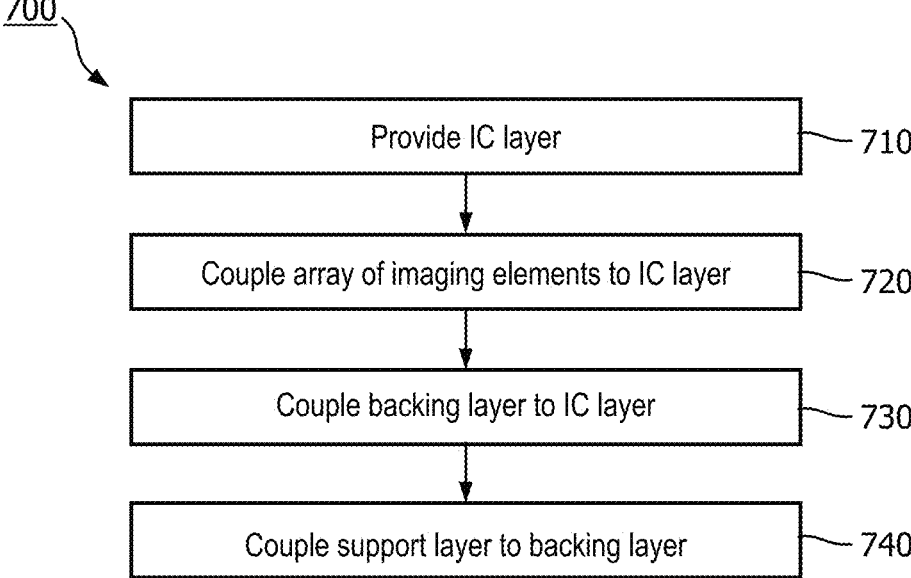
FIG. 7 is a flow diagram of a method of manufacturing the imaging component according to embodiments of the present disclosure.

FIG. 7 is a flow diagram of a method 700 of manufacturing the imaging component 500 according to embodiments of the present disclosure. It is understood that additional steps can be provided before, during, and after the steps of method 700, and some of the steps described can be replaced or eliminated for other embodiments of the method. The steps of the method 700 can be carried out by a manufacturer of a catheter in the order as shown or in any suitable order.

At step 710, the method 700 includes providing an IC layer (e.g., the IC layer 520). The IC layer can be constructed from a first material (e.g., silicon). At step 720, the method 700 includes coupling an array of ultrasound transducer elements (e.g., the ultrasound transducer elements 512) to the IC layer. At step 730, the method 700 includes coupling a backing layer (e.g., the backing layer 530) to the IC layer opposite the array of ultrasound transducer elements. At step 740, the method 700 includes coupling a support layer (e.g., the support layer 540) to the backing layer opposite the IC layer. The support layer can be constructed from a second material similar to or the same as the first material. Thus, a CTE difference between the first material of the IC layer and the second material of the support layer can be less than 10 ppm/C. Alternatively, the second material and the first material may be the same material to provide a perfect CTE match. The support layer can balance CTE-based stress in the imaging component. Thus, the backing layer can be constructed from any of the material A, B, and/or C shown in Table 1. For example, the backing layer can be constructed from commonly used backing material such as the material A described in Table 1 without compromising acoustic attenuation performance.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:
a flexible elongate member comprising a distal portion and a proximal portion, wherein the flexible elongate member comprises an outer diameter sized to be positioned inside a patient body; and
an imaging assembly coupled to the distal portion of the flexible elongate member, wherein the imaging assembly comprises:
  an integrated circuit (IC) layer comprising a first material;
  an acoustic layer comprising an array of ultrasound transducer elements, wherein the acoustic layer is coupled to the IC layer;
  a backing layer coupled to the IC layer, wherein the backing layer comprises a second material; and
  a support layer coupled to the backing layer, wherein the support layer comprises a third material, and wherein a coefficient of thermal expansion (CTE) difference between the first material and the third material is less than the CTE difference between the first material and the second material,
wherein the IC layer, the acoustic layer, the backing layer, and the support layer are sized to fit within the outer diameter,
wherein the acoustic layer is a located on a top side of the IC layer and the backing and support layers are located on a bottom side of the IC layer such that:
  the backing layer and the support layer are located on a same side of the IC layer; and
  the IC layer and the support layer are located on opposite sides of the backing layer.

2. The apparatus of claim 1,
wherein the apparatus comprises an intracardiac echocardiography (ICE) catheter configured to be advanced through a vessel of the patient body, and
wherein the ICE catheter comprises the flexible elongate member and the imaging assembly.

3. The apparatus of claim 1, wherein the imaging assembly is configured to be deflected while the imaging assembly is positioned inside the patient body.

4. The apparatus of claim 1, wherein the array of ultrasound transducer elements is planar.

5. The apparatus of claim 1, wherein the array of ultrasound transducer elements comprises between 500 ultrasound elements and 1500 ultrasound transducer elements arranged in a two-dimensional pattern.

6. The apparatus of claim 1, wherein the array of ultrasound transducer elements comprises a fourth material.

7. The apparatus of claim 6, wherein the fourth material comprises a piezoelectric material.

8. The apparatus of claim 1,
wherein the first material comprises a semiconductor material, and
wherein the second material comprises a polymer material.

9. The apparatus of claim 8,
wherein the semiconductor material comprises silicon, and
wherein the polymer material comprises an epoxy.

10. The apparatus of claim 1, wherein the IC layer is configured to at least one:
receive control signals configured to control the array of ultrasound transducer elements to emit ultrasound energy and receive ultrasound echoes; or
transmit electrical signals representative of the ultrasound echoes received by the array of ultrasound transducer elements.

11. The apparatus of claim 1, wherein the first material and the third material are the same.

12. The apparatus of claim 1, wherein the first material and the third material are different.

13. The apparatus of claim 1, wherein a thickness of the support layer is greater than a thickness of the IC layer.

14. The apparatus of claim 1, wherein the backing layer and the support layer being located on a bottom side of the IC layer is configured to allow emission of ultrasound energy and reception of ultrasound echoes on the top side of the IC layer by the array of ultrasound transducer elements.

15. The apparatus of claim 14, wherein the acoustic layer is located directly on the top side on the IC layer such that IC layer is configured to control the array of ultrasound transducer elements.

16. The apparatus of claim of claim 1, wherein the IC layer and the support layer being located on opposite sides of the backing layer is configured to prevent warping of the imaging assembly.

17. The apparatus of claim 1,
wherein the acoustic layer is located directly on the top side on the IC layer,
wherein the backing layer is located directly on the bottom side on the IC layer,
wherein the support layer is located directly opposite to the IC layer such that the IC layer and the support layer are spaced apart by the backing layer.

* * * * *